United States Patent
Miller et al.

(10) Patent No.: US 12,152,227 B2
(45) Date of Patent: Nov. 26, 2024

(54) MULTIPORT PLATE FOR A BIOPROCESS BAG

(71) Applicant: GLOBAL LIFE SCIENCES SOLUTIONS USA LLC, Marlborough, MA (US)

(72) Inventors: Michael Jason Miller, Westborough, MA (US); Hanna-Leena Saukkonen, Marlborough, MA (US)

(73) Assignee: GLOBAL LIFE SCIENCES SOLUTIONS USA LLC, Marlborough, MA (US)

(*) Notice: Subject to any disclaimer, the term of this patent is extended or adjusted under 35 U.S.C. 154(b) by 840 days.

(21) Appl. No.: 16/980,683

(22) PCT Filed: Apr. 17, 2019

(86) PCT No.: PCT/EP2019/059917
§ 371 (c)(1),
(2) Date: Sep. 14, 2020

(87) PCT Pub. No.: WO2019/201990
PCT Pub. Date: Oct. 24, 2019

(65) Prior Publication Data
US 2021/0024864 A1     Jan. 28, 2021

Related U.S. Application Data

(60) Provisional application No. 62/660,295, filed on Apr. 20, 2018.

(51) Int. Cl.
| C12M 3/00 | (2006.01) |
| C12M 1/00 | (2006.01) |
| C12M 1/12 | (2006.01) |

(52) U.S. Cl.
CPC .......... C12M 23/14 (2013.01); C12M 25/06 (2013.01); C12M 37/04 (2013.01)

(58) Field of Classification Search
CPC ...... C12M 23/14; C12M 25/06; C12M 37/04; C12M 23/26; C12M 23/28; C12M 23/50; C12M 1/007
See application file for complete search history.

(56) References Cited

U.S. PATENT DOCUMENTS 5,350,080 A * 9/1994 Brown ................ C12M 99/00
                                                                    604/408
6,086,574 A * 7/2000 Carroll ............... C12M 99/00
                                                                    604/905
(Continued)

FOREIGN PATENT DOCUMENTS

| CN | 201737946 U | 2/2011 |
| CN | 103370273 A | 10/2013 |
(Continued)

OTHER PUBLICATIONS

English translation of Chinese Office Action dated Aug. 29, 2023 from corresponding China Application No. 2019 980026722.5 filed Apr. 17, 2019.

(Continued)

*Primary Examiner* — Nathan A Bowers
(74) *Attorney, Agent, or Firm* — Grogan, Tuccillo & Vanderleeden LLP (57) ABSTRACT

The invention relates to a a single-use flexible bioreactor bag comprising a rigid multiport plate sealed to a side wall of said bioreactor bag, wherein said multiport plate comprises a plurality of ports. The invention further relates to a method of manufacturing the bag and to a method of installing the bag in a rigid support vessel.

19 Claims, 6 Drawing Sheets

(56) References Cited

U.S. PATENT DOCUMENTS

| | | | | |
|---|---|---|---|---|
| 2006/0240546 | A1* | 10/2006 | Goodwin | C12M 23/14 435/289.1 |
| 2008/0149564 | A1* | 6/2008 | Holmes | A61M 1/3692 210/651 |
| 2012/0178153 | A1* | 7/2012 | Feng | C12M 41/32 435/289.1 |
| 2015/0017711 | A1* | 1/2015 | Bennett | C12M 41/44 435/286.2 |
| 2015/0118753 | A1* | 4/2015 | Brau | B01F 33/401 366/101 |
| 2016/0095279 | A1* | 4/2016 | Brown | C12M 23/46 47/66.7 |
| 2016/0281043 | A1* | 9/2016 | Watkins | C12M 41/00 |
| 2016/0298068 | A1* | 10/2016 | Schumacher | C12M 41/34 |
| 2020/0276588 | A1* | 9/2020 | Reinert | C12M 23/28 |

FOREIGN PATENT DOCUMENTS

| | | | |
|---|---|---|---|
| EP | 2829598 A2 * | 1/2015 | ............ C12M 23/00 |
| JP | 201537399 | 2/2015 | |
| JP | 2016537983 | 12/2016 | |
| WO | 2012082974 A1 | 6/2012 | |
| WO | WO2015/077663 A1 | 5/2015 | |

OTHER PUBLICATIONS

International Search Report from corresponding International Application No. PCT/EP2019/059917 dated Jun. 26, 2019.
English translation of Japanese Office Action dated Mar. 6, 2023 from corresponding Japanese Application No. 2020-558019 filed Apr. 17, 2019.

* cited by examiner

MULTIPORT PLATE FOR A BIOPROCESS BAG

CROSS REFERENCE TO RELATED APPLICATIONS

This application is a National Stage of International Application No. PCT/EP2019/059917 filed on Apr. 17, 2019, which claims priority to U.S. Provisional Application No. 62/660,295 filed on Apr. 20, 2018, all of which are hereby incorporated by reference in their entireties.

TECHNICAL FIELD OF THE INVENTION

The present invention relates to the field of single-use bioprocess bags, and more specifically to a multiport plate for a single-use bioreactor bag.

BACKGROUND OF THE INVENTION

Single-use or disposable systems are rapidly increasing in different industries and especially in industries that require use of clean processing equipment and clean rooms, such as in the biopharmaceutical industry. Disposable systems are flexible and cost-effective and cleaning processes may be reduced or eliminated. Traditional systems comprise re-usable wetted parts in fluid contact which are typically built as stainless steel installations (tubes and vessels), which need to be cleaned or sterilized in between processes or batches. Sterilization is typically done by steam sterilization, which requires technical infrastructure and is a complex and time-consuming process. In contrast, disposable components in disposable systems provide surfaces in fluid contact that are preferably pre-sterilized and pre-qualified to all regulatory requirements. Disposable or single-use systems are replaced in between processes to eliminate cleaning and sterilization issues. Due to lower complexity in systems and auxiliary systems, disposable systems are therefore easy to adapt to different production purposes and facilities. Further, it is easy and less costly to change a product line compared to traditional equipment. Disposable systems may provide also improved reliability as well as product and operator safety in biopharmaceutical processing.

There are several kinds of disposable systems, such as bioreactors, in which disposable containers or bags are used. These containers or bags comprise often sheets of flexible material, such as plastic, plastic laminates or corresponding materials. A flexible bioprocess bag refers to a bag or pouch made of walls of similar structure preferably assembled by welding. These walls may be made of a mono or multilayer film including or not a barrier layer based on a barrier polymer like ethylene vinyl alcohol polymer (EVOH). Generally, these films may have an inner layer (in contact with the contents of the bag when filled) based on a polyolefin, preferably an ultra-low density polyethylene, pref. medical grade (ULDPE). The bag may be of cylindrical shape. Although cylindrical flexible bioprocess bags are difficult to manufacture, the cylindrical shape can be approximated and achieved by welding of multiple film panels of suitable size and shape. However, the flexible bioprocess bags can equally have cubic or parallelepiped shape. Various processing and pre-conditioning steps need to be performed within these bags such as for example pre-sterilization.

One type of mixing system in which such containers or bags can be used is a bioreactor system in which cells or microorganisms can grow. Here, the bags are provided as closed and pre-sterilized components in order to avoid any contamination or inhibition in the growth of the microorganisms or cells intended for cultivation in the bioreactor.

Mixing systems may comprise a support or vessel which supports or houses a disposable bag or container of the above-mentioned type. Typically, the vessel may also be a tank-type support which has a substantially cylindrical or parallelepiped form, for example substantially circular cylindrical and is made of rigid material such as stainless steel to provide sufficient support for the flexible bioprocess bag or container, for example of a kind used in Xcellerex XDR™ Single-use bioreactors. The Xcellerex bioreactor is an example of a mixing system comprising an active mixing element, here a rotating impeller. The flexible container or bag is placed inside the vessel in an accurate manner so that for example different pipelines or tubes, mixers and sensors can be connected to the bag properly and accurately. WO 2005/118771 A2 discloses a disposable system of this kind. Usually, a bioreactor bag has many ports for connection of various tubing and sensors. These ports are typically located on the top of the bag and on a side wall of the bag, where the connections to the side wall ports pass through an opening in the rigid support vessel. The number of ports required can be different for different applications of the bag and during installation of the bag in the vessel, moving the different ports to a position in front of the opening can be complicated.

Hence, there is a need for bags which are easily adapted for different applications and which can easily be installed in rigid support vessels.

SUMMARY OF THE INVENTION

One aspect of the invention is to provide an easily installed single-use bioreactor bag, which can easily be adapted to different cell cultivation applications during manufacturing. This is achieved by a bioreactor bag comprising a rigid multiport plate sealed to a side wall of the bioreactor bag, wherein the multiport plate comprises a plurality of ports. During manufacturing of the bag, different ports can either be fluidically connected to an interior volume of the bag or they can be sealed off from the interior volume. A further advantage of the invention is that multiple ports can be placed at closer distance to each other than when they are separately welded to the bag film.

A further aspect of the invention provides a method of manufacturing the bag discussed above.

A yet further aspect of the invention provides a method of installing the bag discussed above in a rigid support vessel.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical and other changes may be made without departing from the scope of the embodiments. The following detailed description is, therefore, not to be taken as limiting the scope of the invention.

In a first aspect, illustrated by FIGS. 1-6, the invention discloses a single-use flexible bioreactor bag 1 comprising a rigid multiport plate 2 sealed to a side wall 3 of the bioreactor bag. The multiport plate comprises a plurality of ports 4 wherein at least a portion 5 of the plurality of ports can suitably be fluidically connected to an interior volume 8 of the bioreactor bag. The plurality of ports are suitably fluidically connectable to one or more exterior appliances, which can e.g. include supplies of liquids and/or gases, sampling devices, cell separation devices, sensors etc. These connections can be done via fittings 6, e.g. barbed tubing connectors, protruding from the multiport plate e.g. through apertures 7 in the bag side wall. In structural terms, the multiport plate 2 suitably comprises a base plate 19, with an inside 11 and an outside 20. The base plate can e.g. be of rectangular or rounded rectangular shape to fit a window of similar shape in a support vessel, but other shapes, such as oval or circular are also possible. The inside is the side that during use faces the bag interior volume 8 and the outside then faces the bag side wall 3. The plate comprises a plurality of ports 4, each port suitably comprising an opening through the base plate and, extending from the outside 20, a fitting 6 surrounding the opening. The fitting can e.g. be a hose barb connector, but can also be another type of fitting suitable for connecting tubing (e.g. a straight tubular fitting, hose tail or other hose fittings known in the art).

Figure 4:
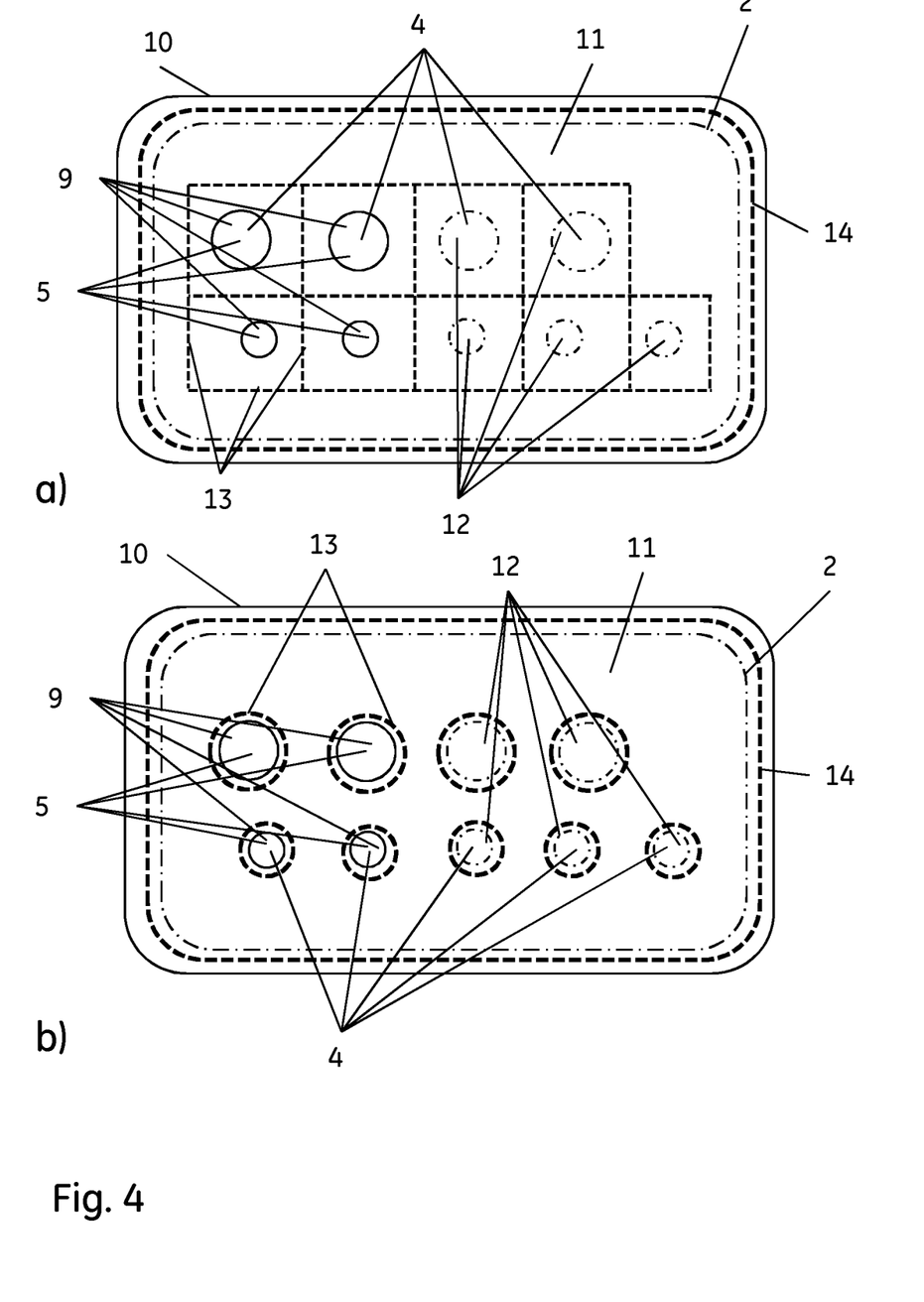
FIG. 4 shows a view from the inside of the bag of a multiport plate in a bioreactor bag of the invention, with a) square sealing welds around the ports and b) circular sealing welds.

In some embodiments, a portion 5 of the plurality of ports are fluidically connected to an interior volume 8 of the bioreactor bag. The fluidical connection can suitably be via apertures 9 formed in a back film 10 covering an inside 11 of the multiport plate, i.e. the side facing the bag interior volume, in registry with ports 5 in the multiport plate. For ports 12 which are not intended to be used, no apertures are formed, leaving the back film sealing off these ports. The back film can then be sealed 13 to the multiport plate around each aperture to prevent cross-talk between the ports and to avoid stagnant volumes. As shown in FIGS. 4 *a*) and *b*), the seals may e.g. be rectangular or circular. A perimeter 14 of the back film can be sealed to the bag side wall, forming a pouch containing the multiport plate. As discussed in the Background section, the bag may then be assembled by welding together a number of film panels, including the side wall panel 3 comprising the multiport plate.

The sealing of the back film to the multiport plate and to the bag side wall can suitably be done by welding to avoid the use of adhesives that may produce undesirable leachables. To facilitate the welding, the multiport plate and both sides of the back film can be made from materials that are weldable to each other and to the inside of the bag film. Suitably, they can comprise polyethylene or ethylene copolymers such as ethylene-vinyl acetate (EVA), either alone or in the form of blends with e.g. cycloolefin copolymers (COC). All materials preferably meet the USP VI requirements for biocompatibility.

Figure 1:
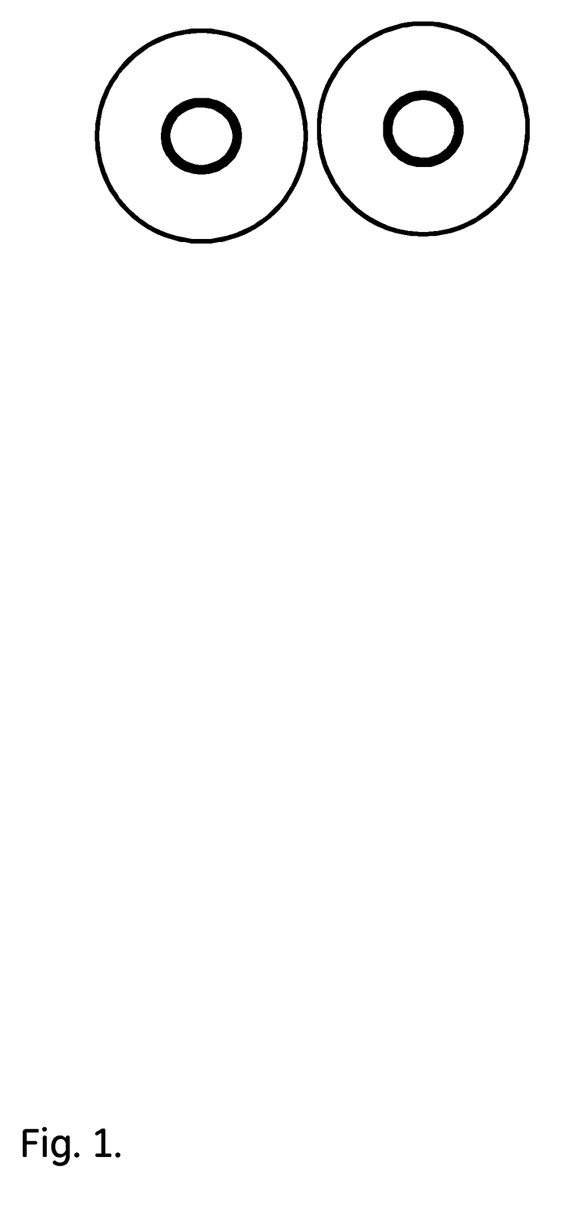
FIG. 1 shows two prior art single ports mounted side by side.
Figure 2:
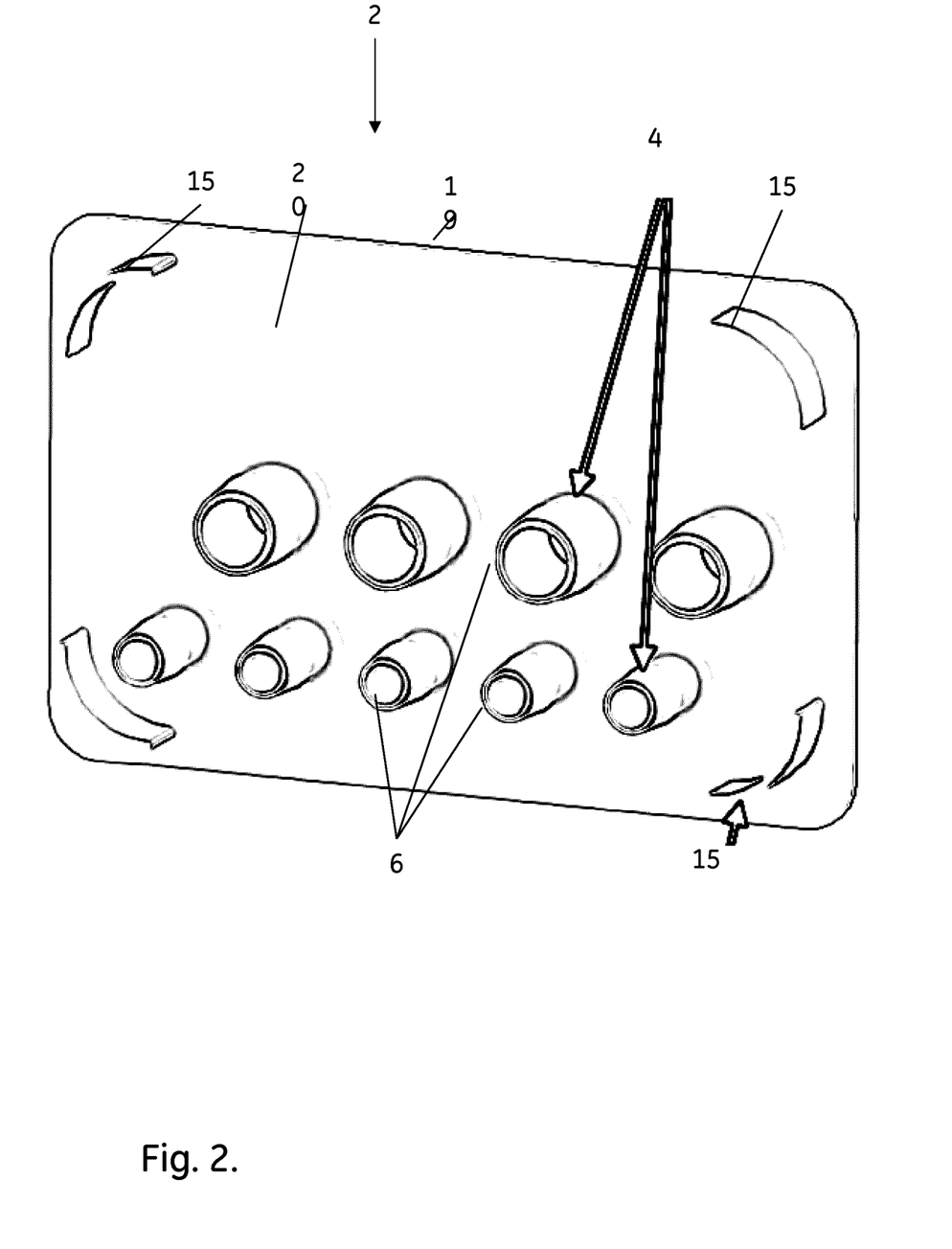
FIG. 2 shows a multiport plate of the invention.
Figure 3:
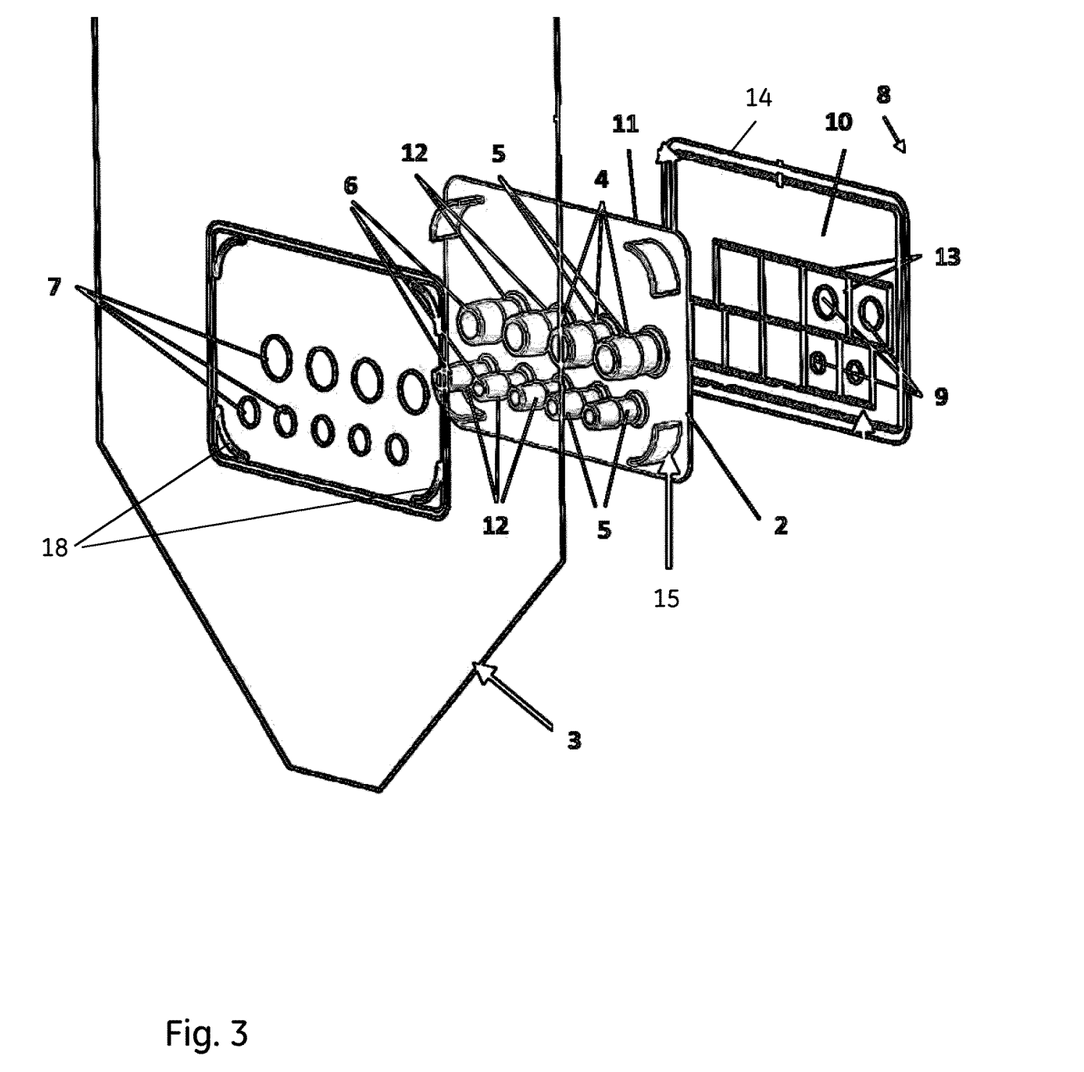
FIG. 3 shows the mounting of a multiport plate in a bioreactor bag of the invention.
Figure 5:
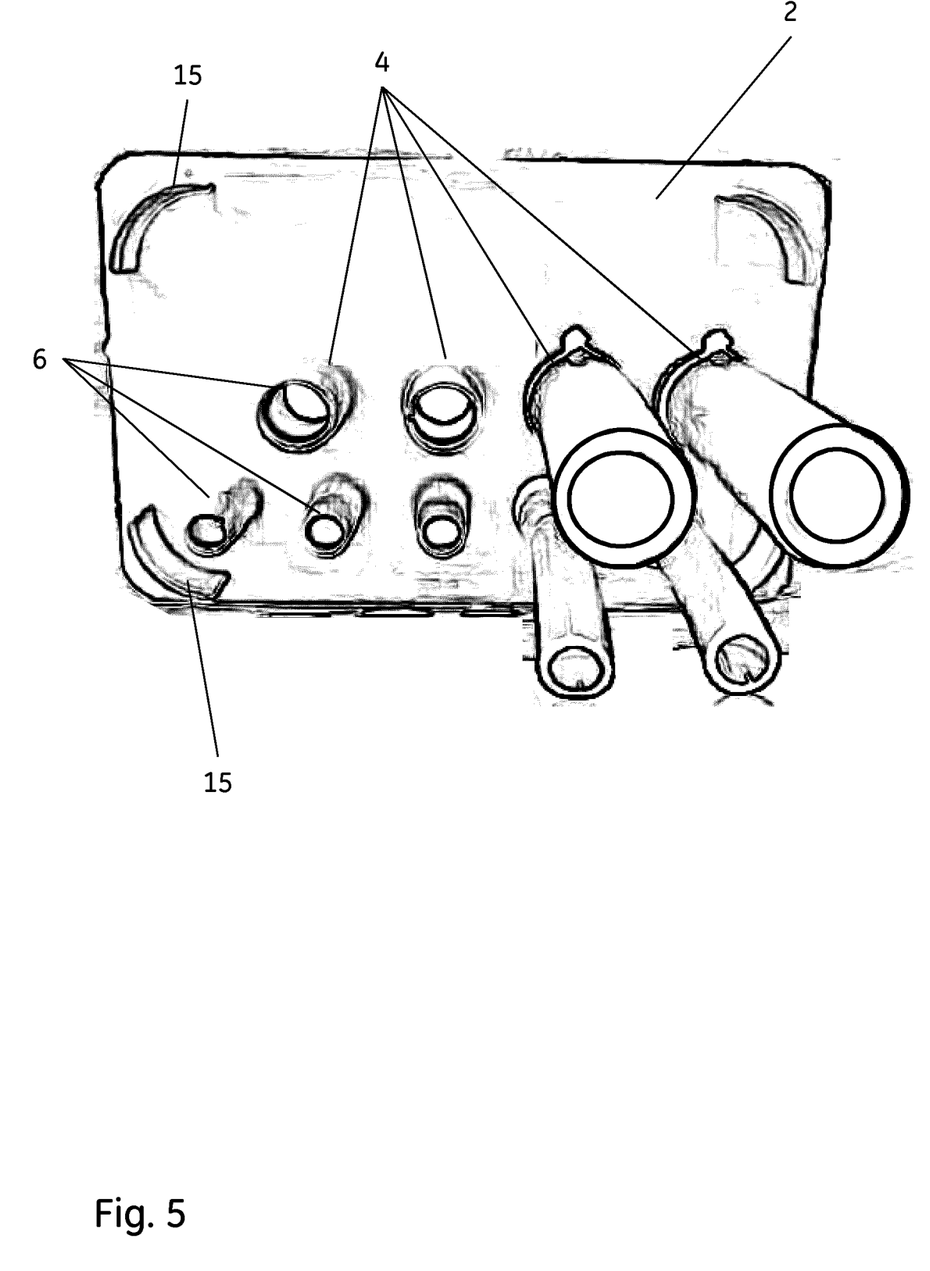
FIG. 5 shows a photograph of a prototype multiport plate, with tubing connected to four of the ports.
Figure 6:
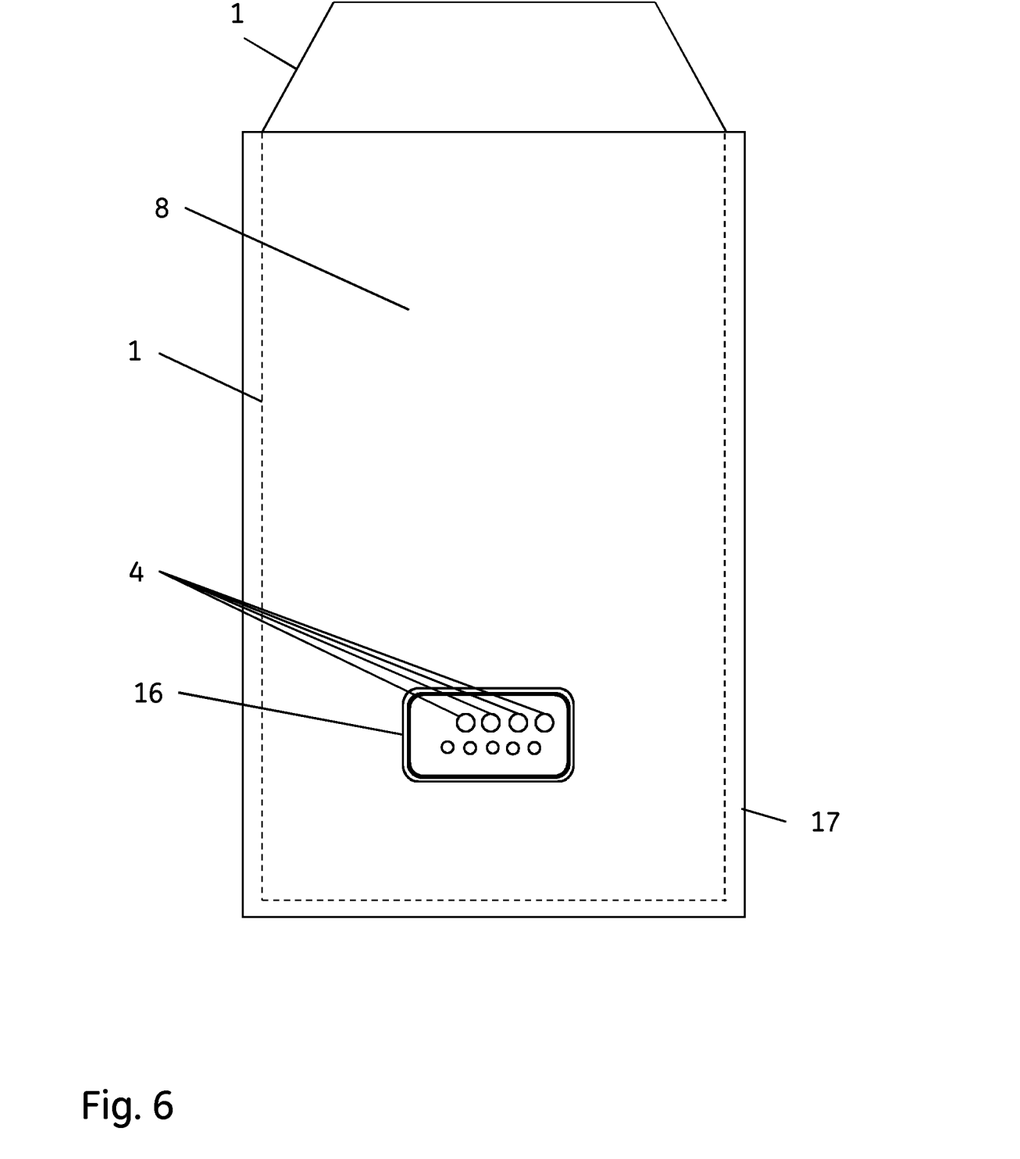
FIG. 6 shows a rigid support vessel with a bioreactor bag of the invention.

The multiport plate may further comprise one or more guides 15 for fitting the plate in a window 16 (also known as an alcove or opening) of a rigid support vessel 17. As shown in FIGS. 2, 3 and 5, the guides 15 can e.g. be ridges or ribs extending from an outer surface of the multiport plate and arranged to mate with the frame of the window 16. The guides may further comprise snap fit elements (not shown) for easy attachment to the window. Suitably, the guides protrude through slits or openings 18 formed in the side wall of the bag.

In a second aspect, the invention provides a method of manufacturing the bioreactor bag as discussed above. This method comprises the steps of:
a) providing a plurality of bag wall panels, a multiport plate and a back film;
b) forming (e.g. punching) a set of apertures in a bag wall panel, corresponding to port fittings of the multiport plate;
c) forming (e.g. punching) a set of apertures in the back film in registry with a portion of the ports in the multiport plate;
d) sealing (e.g. welding) the back film to the multiport plate around the apertures in the back film;
e) mounting the multiport plate on the inside of the bag wall panel, with the port fittings of the plate protruding through the apertures in the bag wall panel;
f) sealing (e.g. welding) the perimeter of the back film to the inside of the bag wall panel;
g) assembling the bioreactor bag by welding the plurality of bag wall panels together.

In some embodiments, the multiport plate may comprise one or more guides for fitting the plate in a window of a rigid support vessel. In this case, step c) may further comprise forming (e.g. punching or cutting) a set of slits or openings for the guides in the bag wall panel and in step e) the guides protrude through the slits or openings.

In a third aspect, the invention provides a method of installing the bag as discussed above in a rigid support vessel. This method comprises the steps of:
a) providing a bioreactor bag as discussed above and a rigid support vessel comprising a window;
b) mounting the bioreactor bag in the rigid support vessel, with the multiport plate facing the window.

If the multiport plate comprises guides for fitting the plate in the window, step c) may further comprise mating the guides with a frame of the window. If the guides comprise snap fit elements, step c) may also comprise snap-fitting the multiport plate into the window frame.

This written description uses examples to disclose the invention, including the best mode, and also to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:
1. A single-use flexible bioreactor bag, comprising:
a rigid multiport plate sealed to an inside of a side wall of said bioreactor bag, wherein said multiport plate comprises an outside surface facing the side wall of said bioreactor bag, an inside surface opposing said outside surface facing an interior volume of said bioreactor bag and a plurality of preformed plate apertures extending between said outside surface and said inside surface, wherein said outside surface comprises a plurality of ports configured to extend outward through said side wall of said bioreactor bag; and a back film coupled to said inside surface of said multiport plate, said back film having a plurality of preformed back film apertures aligned correspondingly with the plurality of preformed plate apertures in said multiport plate, wherein the plurality of preformed back film apertures are separate and distinct from the plurality of preformed plate apertures.

2. The bioreactor bag of claim 1, wherein said plurality of ports are fluidically connectable to one or more external appliances.

3. The bioreactor bag of claim 1, wherein a portion of said plurality of ports are fluidically connected to the interior volume of said bioreactor bag.

4. The bioreactor bag of claim 3, wherein said portion of the plurality of ports are fluidically connected to the interior volume of said bioreactor bag via said plurality of back film apertures formed in said back film covering said inside surface of said multiport plate.

5. The bioreactor bag of claim 4, wherein said back film is sealed around each of said plurality of plate apertures.

6. The bioreactor bag of claim 1, wherein a perimeter of said back film comprises a perimeter portion sealed to said side wall, wherein said perimeter comprises a pouch configured to contain said multiport plate therein.

7. The bioreactor bag of claim 2, wherein a portion of the plurality of ports comprises a lower number of ports than a total number of the plurality of ports.

8. The bioreactor bag of claim 1, wherein one or more ports in said multiport plate are sealed off from the interior of said bioreactor bag by said back film.

9. The bioreactor bag of claim 1, wherein an inside of said side wall comprises polyethylene or an ethylene copolymer, said back film comprises polyethylene or an ethylene copolymer on both sides of said back film, and said multiport plate comprises polyethylene or an ethylene copolymer.

10. The bioreactor bag of claim 1, wherein said multiport plate comprises one or more guides on said outside surface for mounting in a window of a rigid support vessel for supporting said bioreactor bag.

11. The bioreactor bag of claim 10, wherein said guides protrude through openings in said side wall.

12. The bioreactor bag of claim 10, wherein said guides comprise snap fit attachments arranged for engaging said window.

13. A method of manufacturing a single-use bioreactor bag, comprising the steps of:
a) providing a plurality of bag wall panels, a multiport plate and a back film, said multiport plate comprising an outside surface configured to face a side wall of one of said bag wall panels, an inside surface opposing said outside surface configured to face an interior volume of said bioreactor bag and a plurality of preformed plate apertures extending between said outside surface and said surface, wherein said outside surface comprises a plurality of ports and corresponding fittings for the ports configured to extend outward through said one of said bag wall panels;
b) forming a set of apertures in said one of said bag wall panels, corresponding to said port fittings of the multiport plate;
c) forming a set of back film apertures in the back film in registry with a portion of the ports in the multiport plate via the plurality of plate apertures, wherein the set of formed back film apertures are separate and distinct from the set of formed apertures in said one of said bag wall panels;
d) sealing the back film to the multiport plate around the formed back film apertures in the back film;
e) mounting the multiport plate on an inside of said one of said bag wall panels, with the port fittings of the plate protruding through the plurality of plate apertures in the bag wall panel;
f) sealing a portion of a perimeter of the back film to the inside of said one of said bag wall panels;
g) assembling the bioreactor bag by welding the plurality of bag wall panels together;
wherein the multiport plate is sealed to an inside of the bioreactor bag on said one of said bag wall panels.

14. The method of claim 13, wherein the multiport plate comprises one or more guides on the outside surface for fitting the plate in a window of a rigid support vessel, step c) further comprises forming a set of slits or openings for the guides in said one of said bag wall panels and wherein in step e) the guides protrude through the slits or openings.

15. The method of claim 13, wherein said perimeter of said back film comprises a pouch configured to contain said multiport plate therein.

16. A method of installing a single-use bioreactor bag in a rigid support vessel, comprising the steps of:
a) providing the bioreactor bag and a rigid support vessel comprising a window;
b) providing a multiport plate and a back film for use with the bioreactor bag and the rigid support vessel, wherein said multiport plate comprises an outside surface configured to face a side wall of said bioreactor bag, an inside surface opposing said outside surface configured to face an interior volume of said bioreactor bag and a plurality of preformed plate apertures extending between said outside surface and said surface, said outside surface comprising a plurality of ports configured to extend outward through said side wall of said bioreactor bag, wherein said back film comprises a plurality of preformed back film apertures aligned correspondingly with the plurality of preformed plate apertures in said multiport plate, wherein the plurality of preformed back film apertures are separate and distinct from the plurality of preformed plate apertures; and
c) mounting the bioreactor bag in the rigid support vessel, with the multiport plate facing the window, wherein the multiport plate is sealed to an inside of said side wall of the bioreactor bag.

17. The method of claim 16, wherein the multiport plate comprises guides on the outside surface for fitting the plate in the window and the method further comprising step d) of mating the guides with a frame of the window.

18. The method of claim 17, wherein the guides comprise snap fit elements and wherein step d) comprises snap-fitting the multiport plate into the frame of the window.

19. The method of claim 16, wherein a perimeter of said back film comprises a perimeter portion sealed to said side wall, wherein said perimeter comprises a pouch configured to contain said multiport plate therein.

* * * * *